(12) United States Patent
Silva et al.

(10) Patent No.: US 7,025,751 B2
(45) Date of Patent: Apr. 11, 2006

(54) TWO-LUMEN CATHETER FOR DISTAL PROTECTION IN PERCUTANEOUS CORONARY AND PERIPHERICAL INTERVENTION

(76) Inventors: Pedro Silva, Via Bizzoni S, Milan (IT) 20125; Paolo Cremascoli, Via Nievo 8, Milano (IT) 20145

( * ) Notice: Subject to any disclaimer, the term of this patent is extended or adjusted under 35 U.S.C. 154(b) by 88 days.

(21) Appl. No.: 10/462,079

(22) Filed: Jun. 13, 2003

(65) Prior Publication Data

US 2004/0116900 A1    Jun. 17, 2004

(30) Foreign Application Priority Data

Dec. 17, 2002    (IT) .......................... MI2002A2666

(51) Int. Cl.
*A61M 25/00* (2006.01)
(52) U.S. Cl. ..................................... 604/264
(58) Field of Classification Search ................ 604/523, 604/164.13, 164.01, 164.06, 528, 529; 600/585
See application file for complete search history.

(56) References Cited

U.S. PATENT DOCUMENTS

| | | | | |
|---|---|---|---|---|
| 4,014,333 | A | * | 3/1977 | McIntyre ...................... 604/43 |
| 4,904,238 | A | * | 2/1990 | Williams ...................... 604/43 |
| 5,078,701 | A | * | 1/1992 | Grassi et al. ................ 604/264 |
| 5,100,390 | A | * | 3/1992 | Lubeck et al. .............. 604/158 |
| 5,718,678 | A | * | 2/1998 | Fleming, III ................. 604/43 |
| 5,928,186 | A | * | 7/1999 | Homsma et al. .............. 604/22 |
| 5,968,008 | A | * | 10/1999 | Grams .......................... 604/35 |
| 6,332,877 | B1 | * | 12/2001 | Michels ...................... 604/263 |
| 6,488,662 | B1 | * | 12/2002 | Sirimanne .............. 604/164.01 |
| 6,537,294 | B1 | * | 3/2003 | Boyle et al. ................ 606/200 |
| 2002/0072767 | A1 | * | 6/2002 | Zhu ............................ 606/213 |
| 2003/0023263 | A1 | * | 1/2003 | Krolik et al. ............... 606/200 |

* cited by examiner

*Primary Examiner*—Manuel Mendez
(74) *Attorney, Agent, or Firm*—Hedman & Costigan

(57) ABSTRACT

A two-lumen catheter for distal protection in percutaneous coronary and peripherical intervention comprises a tubular body defining a first lumen for allowing a guide wire to pass therethrough and a second lumen for connection to a sucking assembly, and being characterized in that said catheter further comprises an end portion defining tapering portion between the tubular body and the catheter tip, in said tapering portion being provided at least a hole communicating with the second lumen.

6 Claims, 7 Drawing Sheets

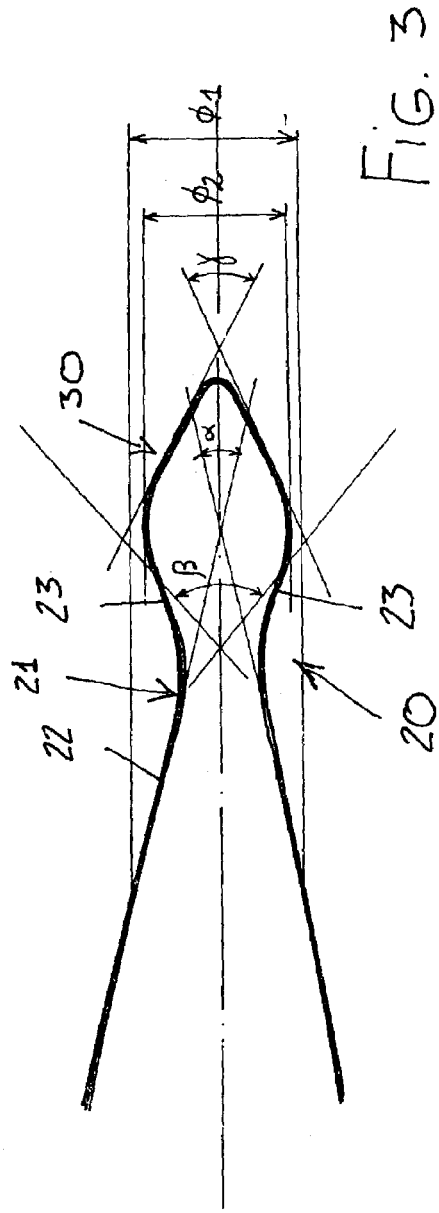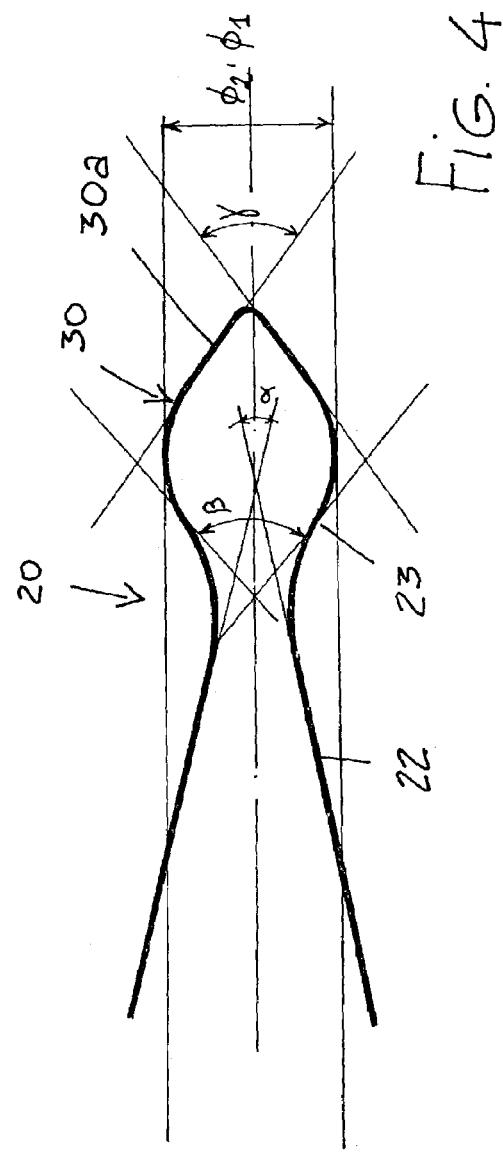

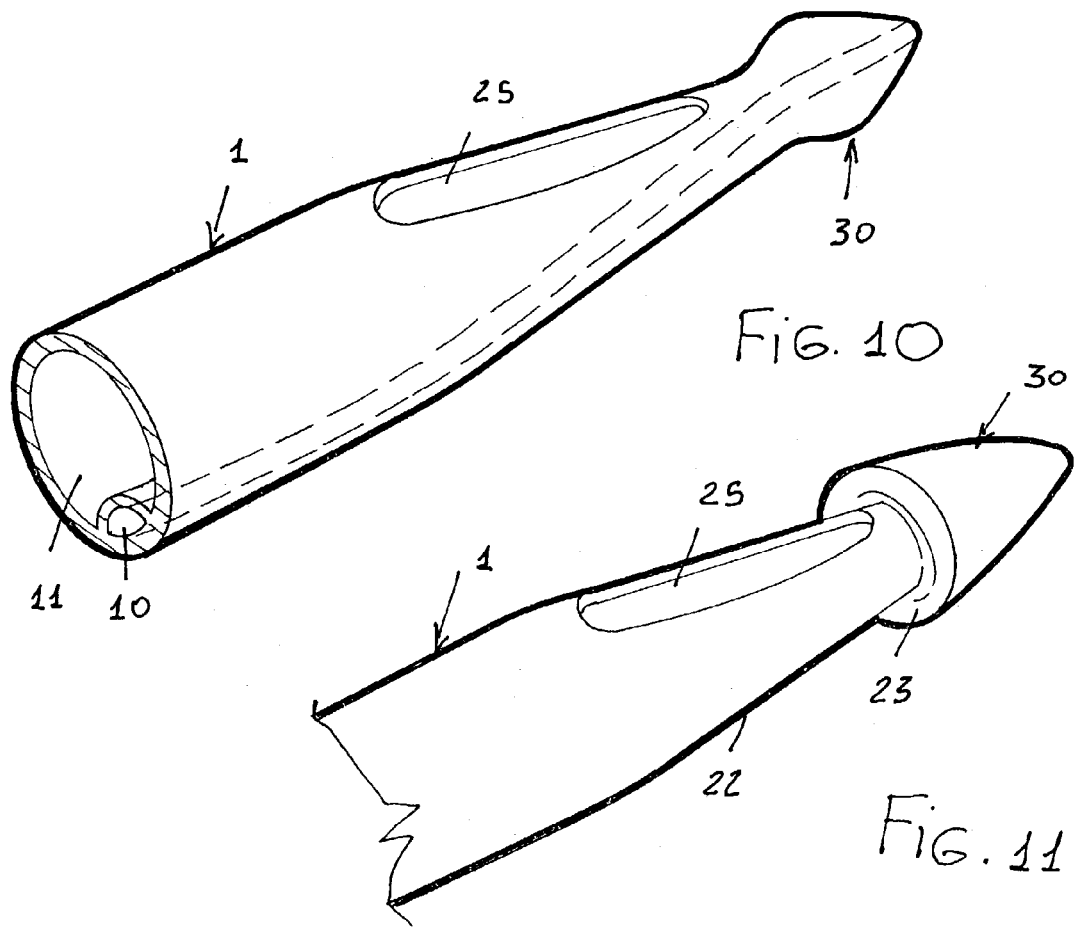
Fig. 10
Fig. 11
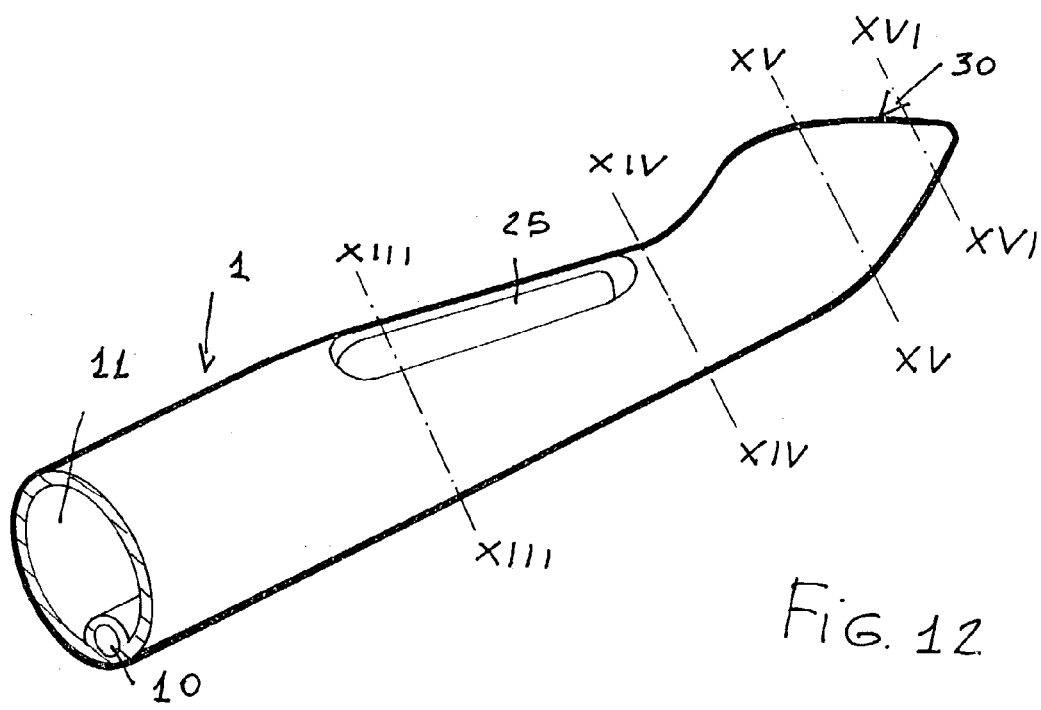
Fig. 12

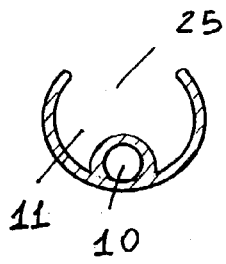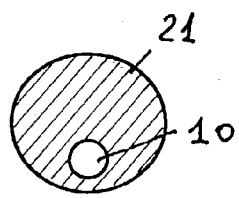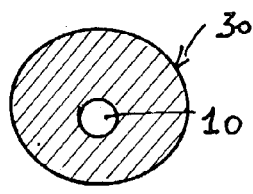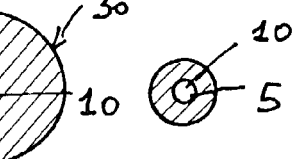
Fig. 13  Fig. 14  Fig. 15  Fig. 16
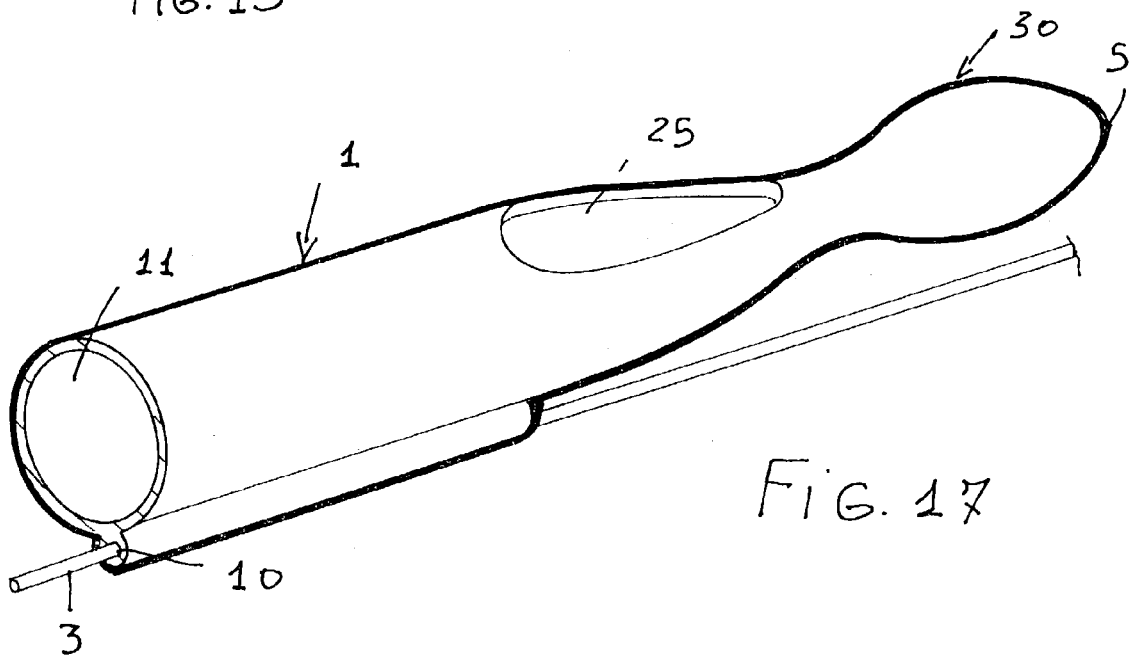
Fig. 17
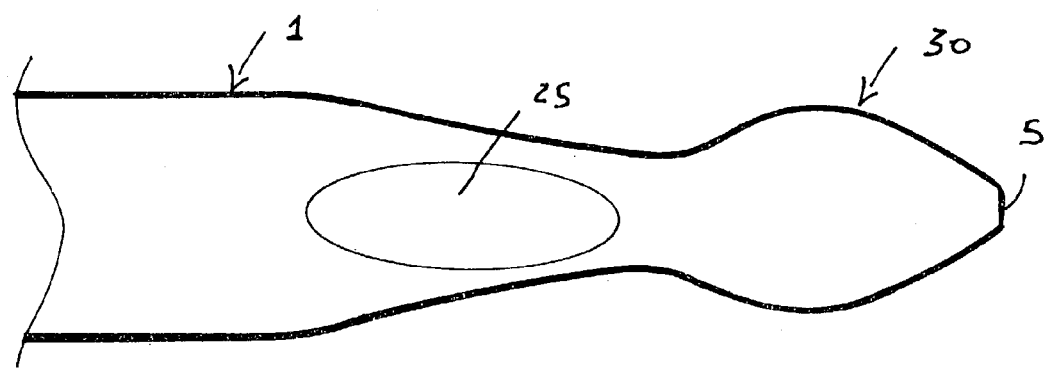
Fig. 18

US 7,025,751 B2

TWO-LUMEN CATHETER FOR DISTAL PROTECTION IN PERCUTANEOUS CORONARY AND PERIPHERICAL INTERVENTION

BACKGROUND OF THE INVENTION

The present invention relates to a catheter to be used in cardiovascular field, more specifically to an aspiration catheter for distal protection in a percutaneous coronary, SVG or saphenous vein graft or peripherical intervention.

Blood vessels are sometimes occluded by plaques or thrombus, this situation is very dangerous to patients health, so often it is necessary to perform medical interventions to remove them.

The percutaneous revascularization interventions, such as angioplasty or stent placement, are to be limited, because they can generate emboli during the procedure. The presence of emboli in the human body is a well-known death or serious injury cause.

So, it has been necessary to develop systems to remove the emboli.

Till now, on the market there is a number of so called protection system, that are substantially composed of occlusion devices or filters that stop and catch the emboli and some dedicated aspiration systems.

These systems are not always useful, due to some difficulties of the procedures that cannot be eluded.

First of all the distal protection intervention must be quick, so the system has to be easy to manipulate and to work; it has to be quickly positioned even if the vessels way is impervious; it positioned even if the vessels way is impervious; it has to perform safely when positioning and also when removing it, it has to work also in very small vessels (less than 4 mm diameter); it has to have the capability of catching large emboli showing the smallest possible encumbrance in the vessel.

The marketed systems are now distant from the above described objectives.

SUMMARY OF THE INVENTION

Accordingly, the aim of the present invention is to provide a two-lumen catheter for distal removal of thrombi by suction, specifically designed for percutaneous coronary surgery operations, and which is very easy and quick to manipulate and to position, because of its simplicity to use.

Within the scope of the above mentioned aim, a main object of the present invention is to provide such a catheter which is totally atraumatic during insertion, use and retraction, because of its body and tip design.

Another object of the present invention is to provide such a catheter which minimizes the detachment from the vessel of the thrombi it meets because of the special tip and hole configuration.

Yet another object of the present invention is to provide such a catheter which is very easy and safe to navigate the vessels because it is centered guided.

Yet another object of the present invention is to provide such a catheter which is compatible with the systems already used during a percutaneous revascularization intervention.

Yet another object of the present invention is to provide such a catheter which is very advantageous from a mere economic standpoint.

According to one aspect of the present invention, the above mentioned aim and objects, as well as yet other objects, which will become more apparent hereinafter, are achieved by a two-lumen catheter, for distal protection, particularly in percutaneous coronary and peripherical intervention, comprising a tubular body defining a first lumen for allowing a guide wire to pass therethrough and a second lumen for connection to a sucking assembly, characterized in that said catheter further comprises an end portion defining a tapering portion, at least a hole communicating with the second lumen being moreover provided.

BRIEF DESCRIPTION OF THE DRAWINGS

Further characteristics and advantages of the present invention will become more apparent hereinafter from the following detailed disclosure of a preferred, though not exclusive, embodiment of a two-lumen catheter for distal protection in percutaneous coronary and peripherical intervention, being illustrated, by way of an indicative, but not limitative, example, in the figures of the accompanying drawings, where:

FIGS. 3 and 4 schematically illustrate a specifically designed pattern for the catheter end portion and clearly showing the design of the catheter tip;

FIG. 10 shows a catheter like that of FIG. 7, with a smaller catheter tip;

FIG. 11 shows a catheter with a different pattern of the catheter tip;

FIG. 12 shows a catheter provided with an asymmetrical catheter tip;

FIG. 13 shows a cross-sectional view substantially taken along the line XIII—XIII of FIG. 12;

FIG. 14 shows a further cross-sectional view substantially taken along the line XIV—XIV of FIG. 12;

FIG. 15 shows a further cross-sectional view substantially taken along the line XV—XV of FIG. 12;

FIG. 16 shows a further cross-sectional view substantially taken along the line XVI—XVI of FIG. 12;

FIG. 17 shows a further embodiment of a catheter having a second outer lumen;

FIG. 18 shows a catheter having an oval-pattern catheter hole.

DESCRIPTION OF THE PREFERRED EMBODIMENTS

Figure 1:
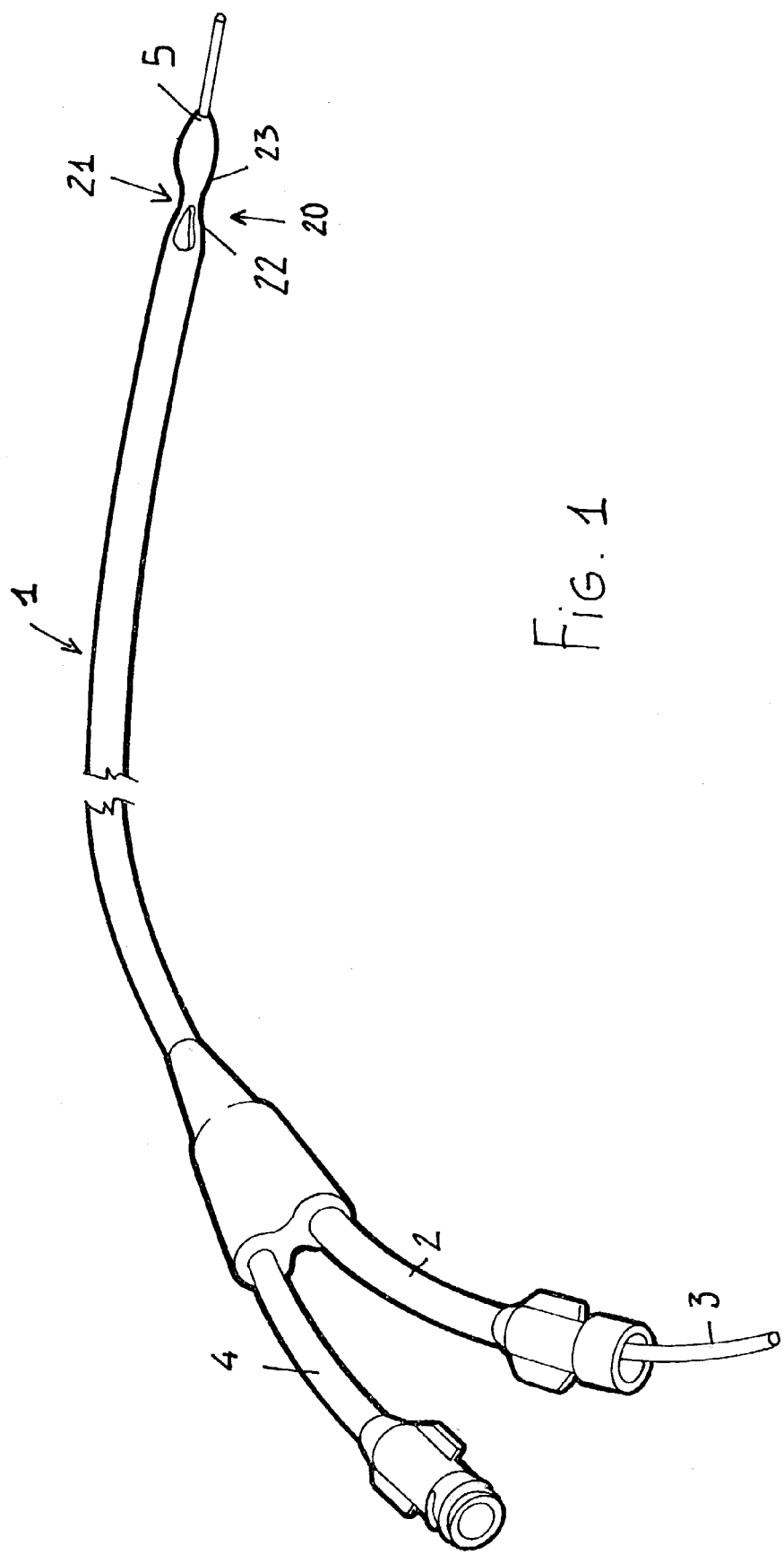
FIG. 1 is a schematic perspective view illustrating a two-inlet catheter.

With reference to the number references of the above mentioned figures, the two-lumen catheter for distal protection, specifically designed for percutaneous and peripherical coronary interventions, according to the present invention, comprises a tubular body 1 which, as is shown in FIG. 1, comprises an inlet 2 for engaging therein a guide wire 3, and a second inlet 4, to be connected to a sucking assembly.

Figure 2:
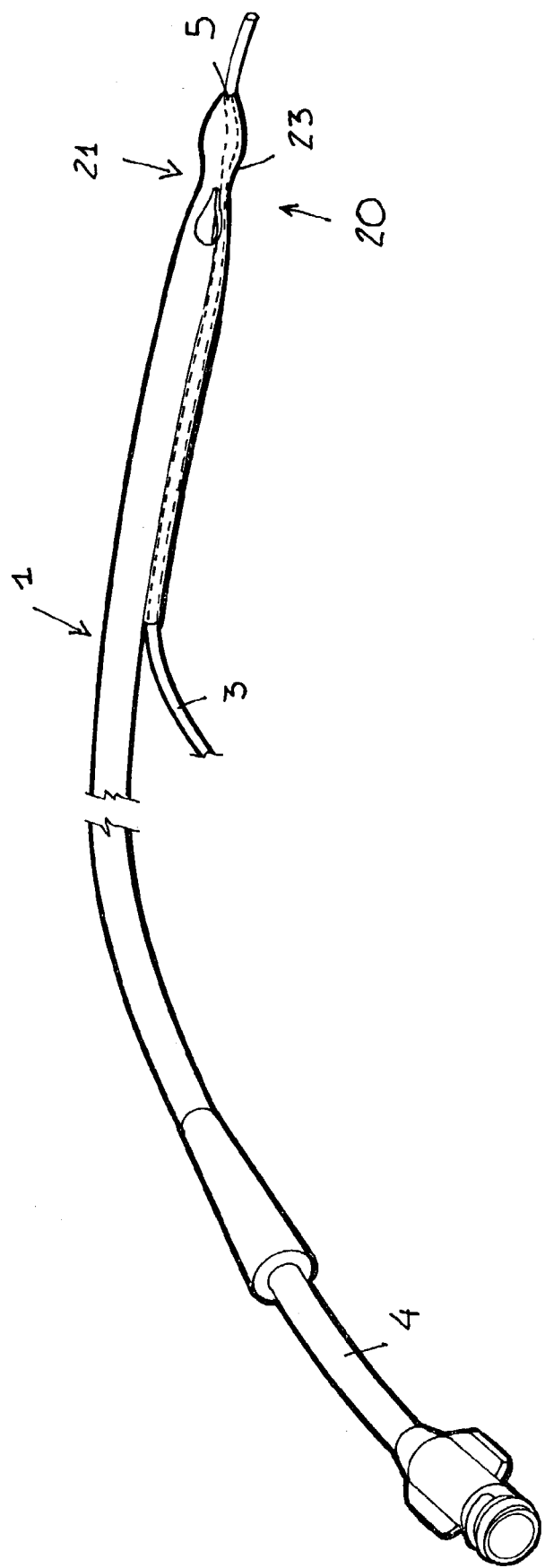
FIG. 2 is a further schematic perspective view illustrating a single-body catheter.
Figure 5:
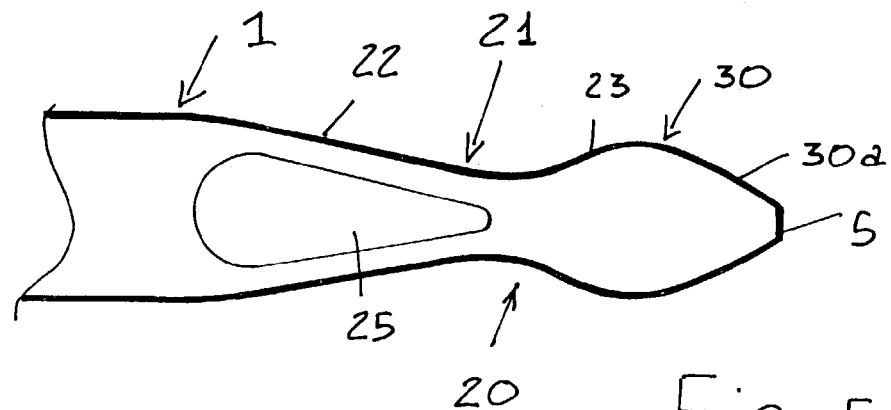
FIG. 5 shows a hole provided through the tapering portion of the catheter.
Figure 6:
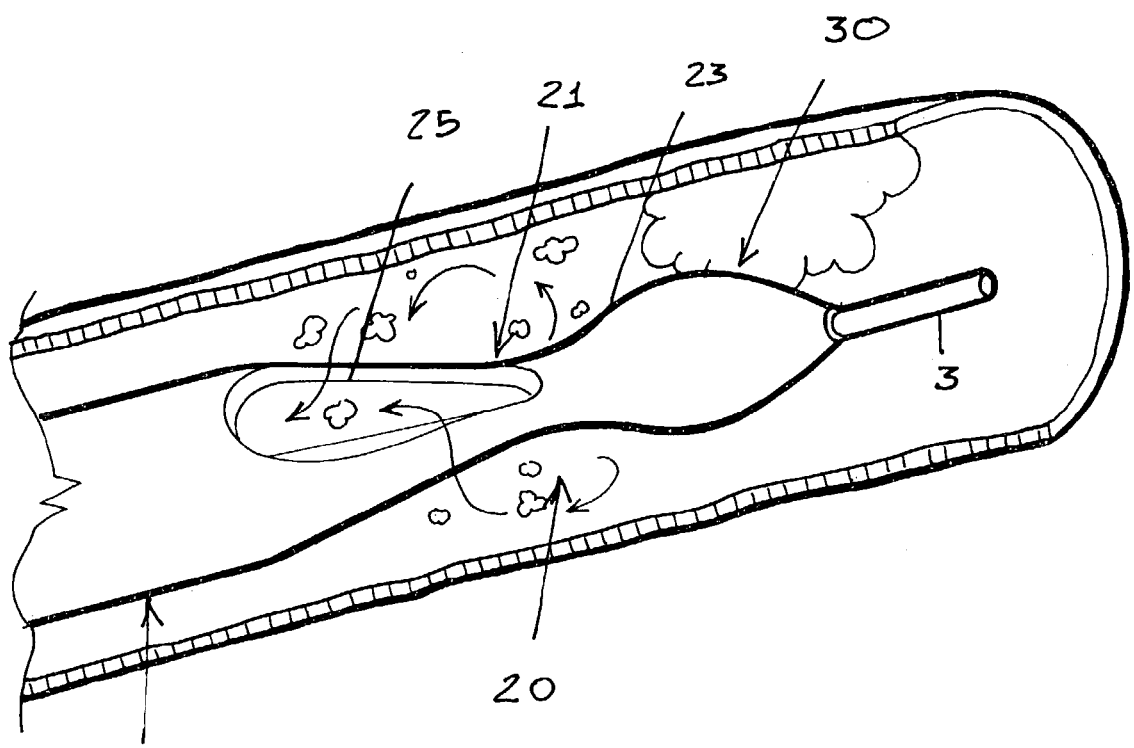
FIG. 6 shows the catheter during the use thereof.

With reference to FIG. 2, it shows a mono-body type of catheter, in which is provided a sucking assembly 4, as axially aligned.

The guide wire, in particular, is engaged in the catheter on the outside and laterally thereof, with respect to the catheter body 1.

The guide wire is typically constituted by a standard metal wire for angioplastic procedures, which has advantageously a size of 0.014 inches.

The guide-wire is centered at the catheter tip, and it exits the catheter through an outlet hole 5, which is coaxially arranged with respect to said catheter tip.

Since the guide is centered at the tip, the catheter can be easily guided in tortuous vessels; moreover, the catheter can advance also in partially occluded vessels, minimizing the risk of detaching occluding substances from it.

The guide wire passes through a first lumen 10 which, depending on the specifically designed embodiments, and as is shown in the drawings, can be arranged inside the tubular body 1, defining a second lumen 11, but it can also be arranged outside of said tubular body 1.

Figure 7:
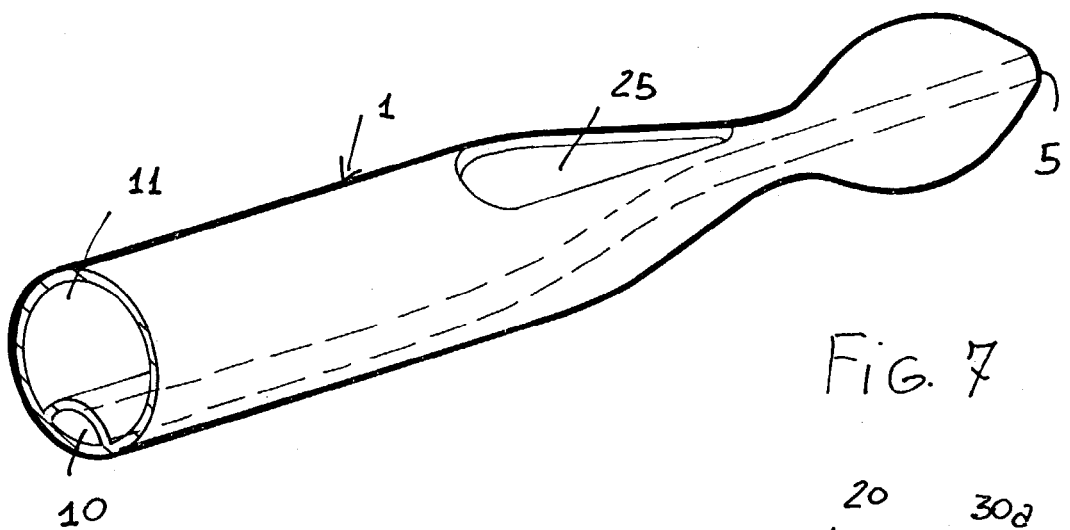
FIG. 7 shows a catheter with the first lumen thereof arranged on the inner periphery of the second lumen thereof.
Figure 8:
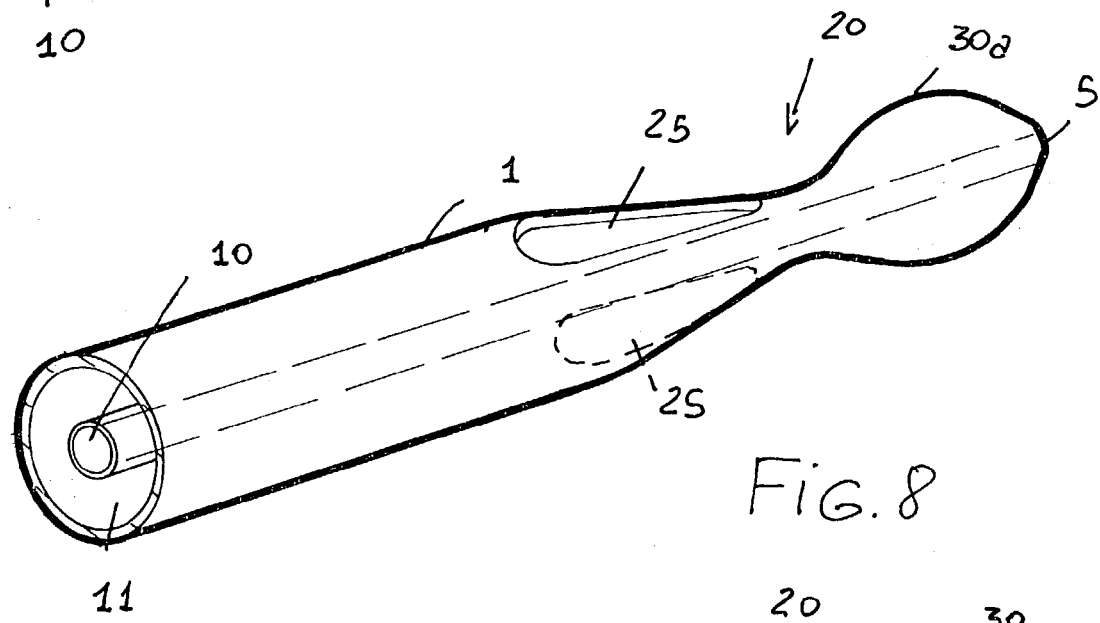
FIG. 8 shows a catheter with the second lumen coaxially arranged.

With reference to FIG. 7, the first lumen 10 is arranged on the inner wall, whereas, with reference to FIG. 8, the first lumen 10 is coaxially arranged with respect to the tubular body 1.

Figure 9:
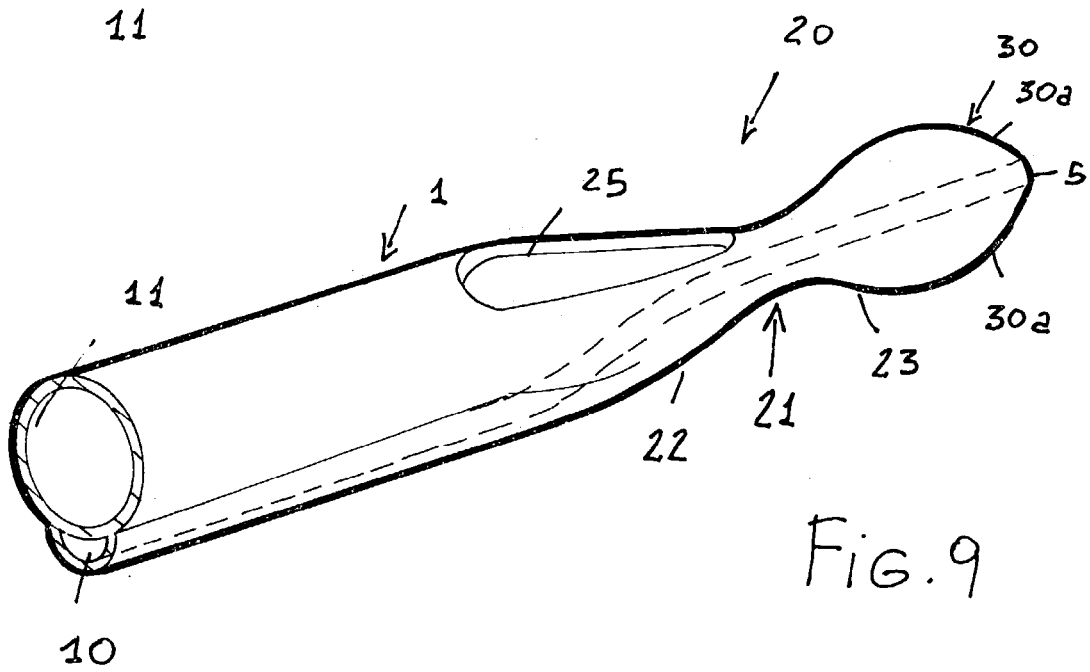
FIG. 9 shows a catheter with the second lumen arranged on the outer surface of the catheter.

FIG. 9 shows an embodiment in which the first lumen 10 is applied to the cuter surface of the tubular body 1.

The second lumen 11 is larger than the first lumen, and is connected to the inlet 4, where it is possible to apply a standard syringe for sucking thrombi.

The sucking, in particular, is performed through the second lumen and can be achieved through a hole which is arranged at the catheter tip.

A main feature of the present invention is that the catheter comprises and end catheter portion, generally indicated by the reference number 20, defining a tapering portion 21 integral with the tubular body, which is arranged between the tubular body 1 and the catheter tip 30 which is integral with the tapering portion and, advantageously, has an ogival pattern.

The tapering portion 21 is defined by a first substantially rectilinear coupling portion 22 for connection to the tubular body 1 and by a second substantially curved and integral coupling portion 23 connecting with and integrally meeting the outer bulged surface of catheter tip.

With reference to FIGS. 3 and 4, it should be apparent that the tapering portion 22 defines an angle $\alpha$, which is less than the angle $\gamma$, defined by the outer portion 30a of the catheter tip, arranged on the opposite side from the fitting tapering portion to the tip 23 defining an angle $\beta$.

In this tapering portion, is provided at least a hole generally indicated by the reference number 25 which, as is shown in FIG. 7, has a drop configuration, with the larger portion thereof facing the tubular body 1.

The tapering portion is tapered, as already stated, according to the angle $\alpha$ which is so designed as to allow the length of the tapering portion to substantially correspond to the same length of the catheter tip.

Moreover, the catheter tip is defined by the above mentioned angles $\beta$ and $\gamma$, which provide a lozenge type of pattern, or, optional an ogival pattern.

On the catheter tip is provided a throughgoing hole 5 in which is engaged the guide wire.

The angle $\gamma$ allows the catheter to be atraumatically and smoothly advanced through stenotic regions, and the front portion of the catheter tip is centered in the vessel and symmetrically slanted to minimize the pushing and/or removing of occluding substances.

The angle $\beta$ has been designed to cause a micro-turbulent blood flow in this region.

In fact, the combination of the tapering portion 21 and drop-shape hole 25, and of the angle $\beta$ of the tip 30, provides a turbulent flow trapping therein thrombus particles, thereby improving their suction through the lumen 25, by a syringe operating through the inlet 4.

The area included between the angle $\alpha$ and angle $\beta$ is sufficiently large, thereby defining the lumen of the tip ending in the hole 5.

Since this area contains only the lumen for the guide wire 3 and since said area is symmetrical, the tip is reinforced and the guide wire is so centered in an enlarged cross section of the catheter, thereby the catheter can easily follow tortuous vessels without kinks.

With respect to FIGS. 3 and 4, it should be apparent that the tapering portion 22 defines, with respect to the longitudinal axis thereof, an angle $\alpha$, which is less than the angle $\gamma$, defined by the outer portion 30a of the catheter tip, arranged on the opposite side from the fitting tapering portion to the tip 23 defining an angle $\beta$.

The diameter of the catheter or tubular body 1 is indicated by $\Phi 1$ and a relationship $\Phi 2 \leq \Phi 1$ advantageously exists there between.

Under this condition, the catheter tip allows the catheter to safely advance through the blood vessel, and, simultaneously, the catheter tip cannot negatively affect the sucking operation.

If $\phi 2$ would be larger than $\phi 1$, then the occluding substances could not be arrived at by the tapering region and, consequently, they could not be sucked.

As is clearly shown in FIG. 8, it is also possible to provide a plurality of holes 25 for connection with the second lumen.

Moreover, with reference to FIG. 10, the catheter can also have a stronger catheter tip 30, with a different application or provision of the angle $\beta$ and of the angle $\alpha$.

With reference to the FIG. 11, the angle $\beta$ larger than 180° provides practically a recess further improving the turbulent movement toward the hole 25.

This type of tip is very flexible or soft, thereby it cannot damage the vessel wall.

FIG. 12 shows and asymmetrical catheter tip having angles $\beta$ and $\alpha$ only toward the region where the hole is provided.

With such an approach, the catheter tip is maximally reinforced, while defining the tapering regions facilitating the use of the catheter.

FIG. 17 schematically shows an embodiment in which the guide wire 3 does not pass through the inside of the catheter tip, and the guide is arranged at the vessel wall.

FIG. 18 shows a hole 25 having an ogival pattern.

The above disclosed catheter can be made by extruding materials which are conventionally used for making angioplastic catheters.

To provide the required improved performance, the area of the tip can be made by coextruding different materials.

Preferably, the catheter tip is softer than the catheter tubular body 1.

Likewise, it is possible to over-mold on the catheter body a softer plastic material.

Moreover, the catheter can be made of a radio-opaque material along its overall length, or this can be achieved by applying a marking element at the distal tip of the catheter.

Furthermore, the catheter can be coated by blood compatible coatings, to improve the pushing characteristics of the catheter and its atrobogeneity.

From the above disclosure it should be apparent that the invention fully achieves the intended aim and objects.

In particular, the invention provides a catheter which can be introduced into a vessel in a very quick and simple manner, while providing the optimum effects deriving from the provision of the tapering portion allowing a thrombus to be easily and efficiently sucked.

The invention, as disclosed, is susceptible to several modifications and variations, all of which will come within the scope of the invention.

Moreover, all the constructional details can be replaced by other technically equivalent elements.

In practicing the invention, the used materials, provided that they are compatible to the intended application, can be any depending on requirements.

The invention claimed is:

1. A two-lumen catheter for distal protection and removing thrombi in peripheral and percutaneous coronary surgery interventions, said two lumen catheter comprising a tubular body defining a first lumen for allowing a guide wire to pass therethrough and a second lumen for coupling to a sucking assembly, said first lumen having a cross-section smaller than a cross-section of said second lumen, wherein said catheter further comprises an end portion defining a tapering portion integral with said tubular body arranged between the tubular body and a catheter tip integral with said tapering portion and having a bulged outer surface, said tapering portion having one or more holes for communicating with said second lumen and a distal end with an outlet hole for allowing said guide wire to coaxially exit said catheter, said tapering portion being defined by a first substantially rectilinear coupling portion integrally connecting to said tubular body and by a second substantially curved coupling portion integrally connecting to and matching with said bulged outer surface of said catheter tip, wherein said tapering portion has a length substantially equal to a length of said catheter tip, and wherein said bulged surface of the catheter tip defines an ogival shape.

2. A catheter, according to claim 1, wherein said catheter tip has a maximum diameter smaller than or equal to a diameter of said tubular body.

3. A catheter, according to claim 1, wherein said at least one of said one or more holes is located on the said first coupling portion of said tapering portion directed toward said tubular body.

4. A catheter, according to claim 1, wherein said one or more holes have a drop pattern with an enlarged portion thereof facing said tapering portion.

5. A catheter, according to claim 1, wherein said catheter tip has an outer diameter much smaller than an outer diameter of said tubular body.

6. A catheter, according to claim 1, wherein said catheter tip defines a recessed portion with an angle greater than 180°.

* * * * *